(12) United States Patent     (10) Patent No.:   US 12,672,825 B2

Zhang et al.     (45) Date of Patent:     Jul. 7, 2026

(54) DEVICES, SYSTEMS AND METHODS OF PELVIC FLOOR MUSCLE EXAMINATION

(71) Applicant: HillMed, Inc., Houston, TX (US)

(72) Inventors: Yingchun Zhang, Katy, TX (US); Nicholas Dias, Houston, TX (US)

(73) Assignees: HillMed, Inc., Houston, TX (US); University of Houston System, Houston, TX (US)

( * ) Notice: Subject to any disclaimer, the term of this patent is extended or adjusted under 35 U.S.C. 154(b) by 904 days.

(21) Appl. No.: 17/836,394

(22) Filed: Jun. 9, 2022

(65) Prior Publication Data

US 2022/0395228 A1     Dec. 15, 2022

Related U.S. Application Data

(60) Provisional application No. 63/208,691, filed on Jun. 9, 2021.

(51) Int. Cl.
    *A61B 5/00*        (2006.01)
    *A61B 5/296*      (2021.01)
            (Continued)

(52) U.S. Cl.
    CPC ............ *A61B 5/6806* (2013.01); *A61B 5/296* (2021.01); *A61B 5/391* (2021.01); *A61B 5/397* (2021.01);
            (Continued)

(58) Field of Classification Search
    CPC ......... A61B 5/296; A61B 5/391; A61B 5/397; A61B 5/4255; A61B 5/4337;
            (Continued)

(56) References Cited

U.S. PATENT DOCUMENTS 11,317,854 B1 *   5/2022   Roberts .................... A61B 8/08
2006/0167564 A1   7/2006   Flaherty et al.
            (Continued)

OTHER PUBLICATIONS

International Search Report and Written Opinion issued by the International Searching Authority in connection with International Application No. PCT/US2022/032800, dated Sep. 2, 2022.

(Continued)

*Primary Examiner* — Alex M Valvis
*Assistant Examiner* — Anna Roberts
(74) *Attorney, Agent, or Firm* — Carter, DeLuca & Farrell LLP; George Likourezos

(57)        ABSTRACT

A glove-mountable system for pelvic floor muscle (PFM) examination includes a first flexible member including a force sensor configured to detect a force applied to a PFM of a patient by a user. A second flexible member includes an electromyography (EMG) electrode, a stimulation electrode, and a 3-D digitization probe. The second flexible member is stacked on the first flexible member and each flexible member is secured to an examination glove. An actuation button is actuated by the user when at least one point of interest is detected in at least on PFM. A computer including a processor and a memory is in communication with the first flexible member, the second flexible member and the actuation button. The computer generates a 3-D map of a plurality of PFMs of the patient based on data received from the first flexible member, the second flexible member and the actuation button.

12 Claims, 9 Drawing Sheets

(51) Int. Cl.

| | |
|---|---|
| *A61B 5/391* | (2021.01) |
| *A61B 5/397* | (2021.01) |
| *A61B 90/00* | (2016.01) |
| *G16H 20/17* | (2018.01) |
| *G16H 40/63* | (2018.01) |
| *G16H 50/50* | (2018.01) |

(52) U.S. Cl.
CPC .......... *A61B 5/4255* (2013.01); *A61B 5/4337* (2013.01); *G16H 20/17* (2018.01); *G16H 40/63* (2018.01); *G16H 50/50* (2018.01); *A61B 2090/064* (2016.02)

(58) Field of Classification Search
CPC ............ A61B 5/6806; A61B 2090/064; G16H 20/17; G16H 20/30; G16H 40/63; G16H 50/20; G16H 50/50
USPC ......................................................... 600/546
See application file for complete search history.

(56) References Cited

U.S. PATENT DOCUMENTS

| | | | |
|---|---|---|---|
| 2013/0019374 A1 | 1/2013 | Schwartz | |
| 2013/0158365 A1* | 6/2013 | Chey ................... | A61B 5/14503 |
| | | | 600/595 |
| 2015/0151122 A1* | 6/2015 | Pelger .................... | A61B 5/391 |
| | | | 607/40 |
| 2020/0230406 A1 | 7/2020 | Brink et al. | |
| 2020/0367823 A1 | 11/2020 | Chahine et al. | |
| 2021/0069513 A1 | 3/2021 | Beer et al. | |
| 2021/0161403 A1* | 6/2021 | Beer .................. | A61B 5/02055 |

OTHER PUBLICATIONS

International Preliminary Report on Patentability issued by the International Bureau of WIPO in connection with International Application No. PCT/US2022/032800, dated Nov. 21, 2023.

* cited by examiner

400

Figure 5A:
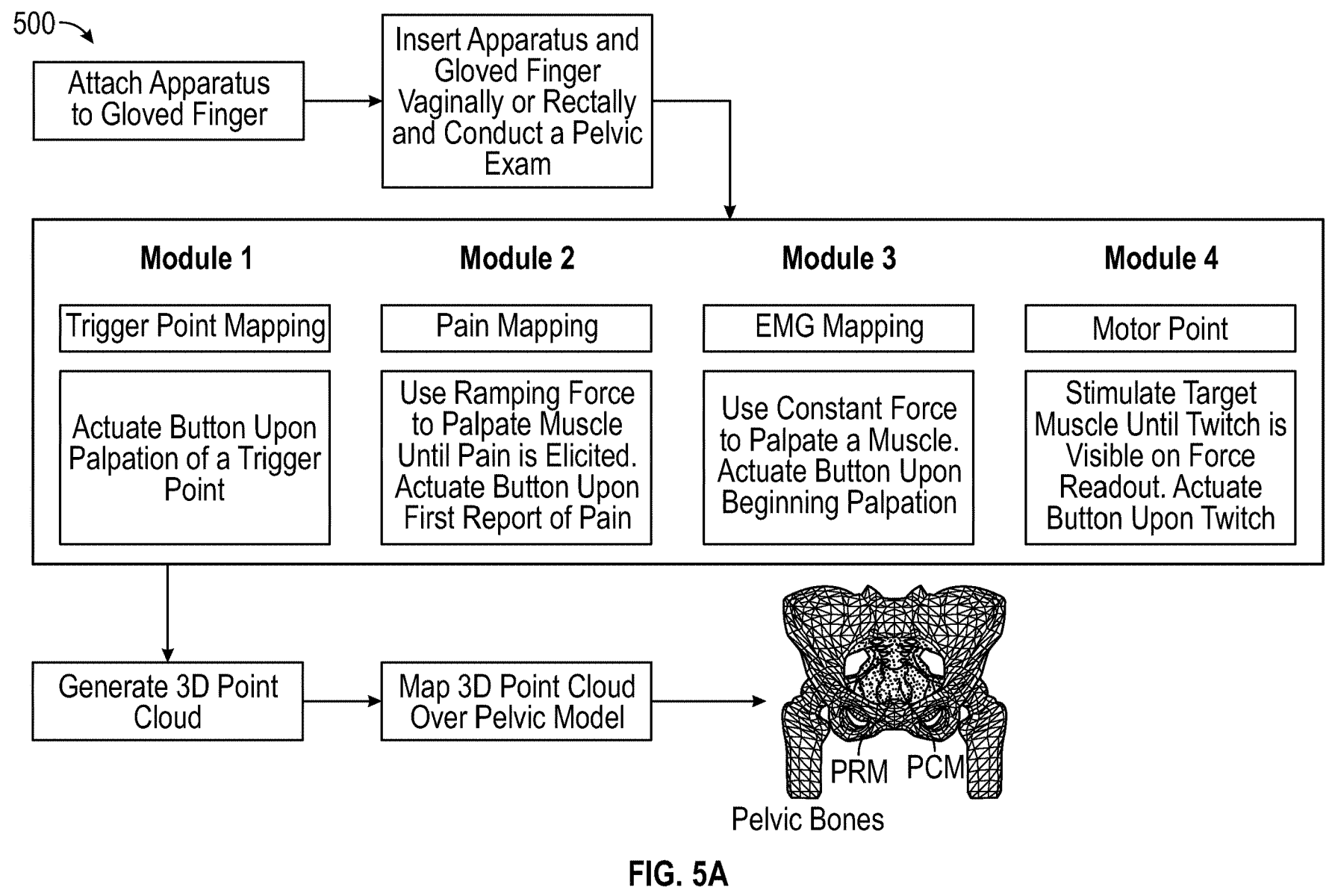

500

Attach Apparatus to Gloved Finger

Insert Apparatus and Gloved Finger Vaginally or Rectally and Conduct a Pelvic Exam

Module 1

Trigger Point Mapping

Actuate Button Upon Palpation of a Trigger Point

Module 2

Pain Mapping

Use Ramping Force to Palpate Muscle Until Pain is Elicited. Actuate Button Upon First Report of Pain

Module 3

EMG Mapping

Use Constant Force to Palpate a Muscle. Actuate Button Upon Beginning Palpation

Module 4

Motor Point

Stimulate Target Muscle Until Twitch is Visible on Force Readout. Actuate Button Upon Twitch Generate 3D Point Cloud Map 3D Point Cloud Over Pelvic Model

PRM  PCM

Pelvic Bones

Figure 6:
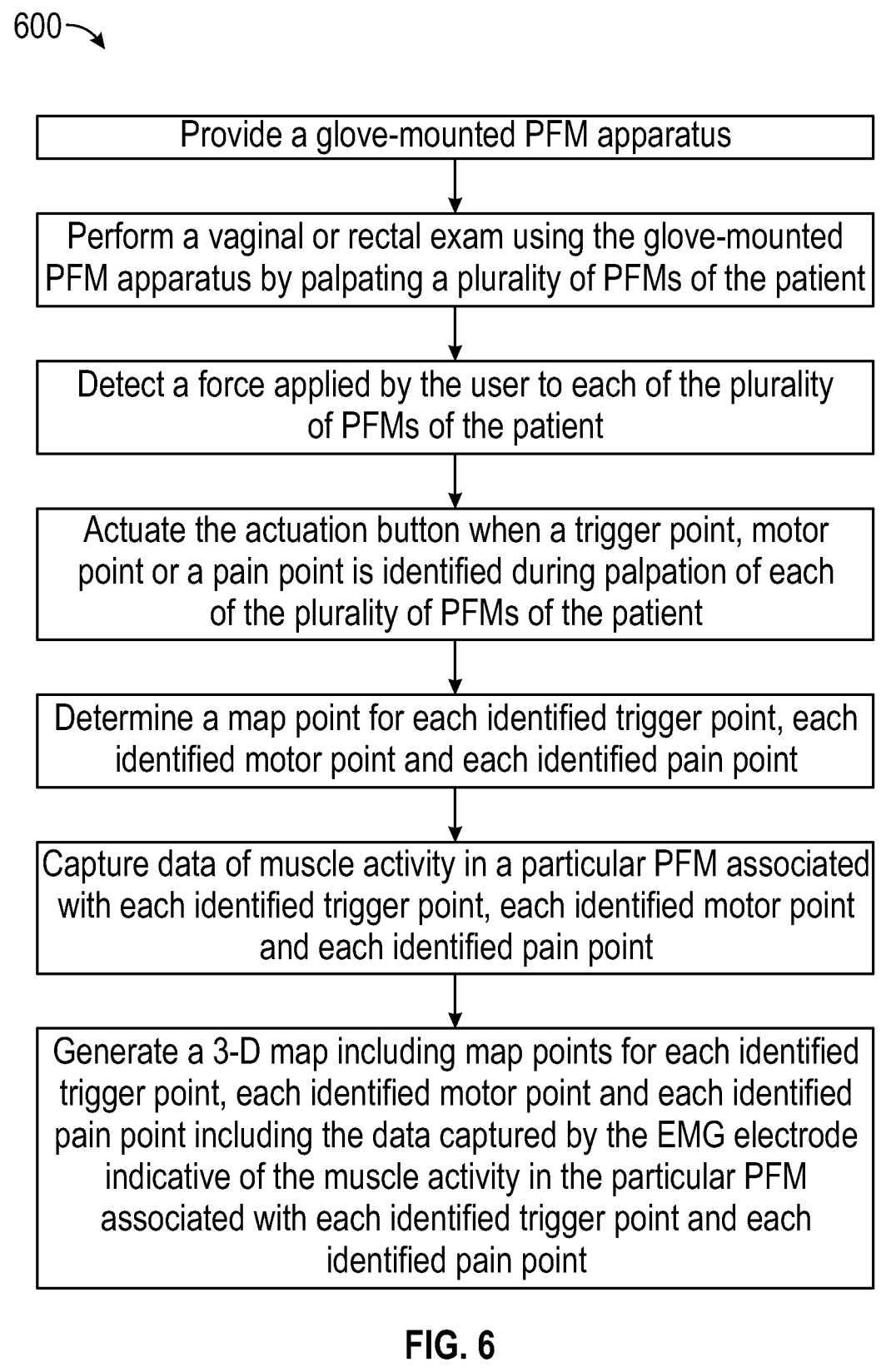

| Provide a glove-mounted PFM apparatus |

| Perform a vaginal or rectal exam using the glove-mounted PFM apparatus by palpating a plurality of PFMs of the patient |

| Detect a force applied by the user to each of the plurality of PFMs of the patient |

| Actuate the actuation button when a trigger point, motor point or a pain point is identified during palpation of each of the plurality of PFMs of the patient |

| Determine a map point for each identified trigger point, each identified motor point and each identified pain point |

| Capture data of muscle activity in a particular PFM associated with each identified trigger point, each identified motor point and each identified pain point |

| Generate a 3-D map including map points for each identified trigger point, each identified motor point and each identified pain point including the data captured by the EMG electrode indicative of the muscle activity in the particular PFM associated with each identified trigger point and each identified pain point |

DEVICES, SYSTEMS AND METHODS OF PELVIC FLOOR MUSCLE EXAMINATION

CROSS REFERENCE TO RELATED APPLICATION

This U.S. Non-Provisional patent application claims priority to U.S. Provisional Patent Application No. 63/208,691, filed on Jun. 9, 2021, the entire contents of which are incorporated by reference herein.

FIELD

The present disclosure relates to pelvic floor muscle (PFM) examination, and more specifically, to devices, systems and methods of Pelvic Floor Muscle (PFM) examination.

BACKGROUND

The PFMs are skeletal muscles that include two primary layers. The first, most superficial layer, is composed of the bulbospongiosus and ischiocavernosus muscles. The bulbospongiosus muscles provide some support for the pelvic organs, but its primary function is related to support of sexual function and micturition. Specifically, the bulbospongiosus maintains erection and facilitates ejaculation in men, and supports the perineal body in women. The ischiocavernosus muscle, similarly, supports erection in men and contracts the vaginal wall during orgasm in women. Contrarily, the deep PFM, including the levator ani, iliococcygeus, and coccygeus muscles, are integrally crucial in managing the pelvic organs' support a result, the maintenance of urinary and fecal continence. The levator ani can further be divided into the puborectalis and pubococcygeus muscles. The levator ani muscles have been shown to contribute the most to the support of the pelvic organs. The pubococcygeus has its origin in the pubic symphysis and inserts into the anterior sacrococcygeal ligament. The puborectalis shares its origin with the pubococcygeus at the pubic symphysis but terminates at a "sling" behind the rectum.

The PFMs differ from most skeletal muscles in that they constantly exhibit tonic motor unit activity at rest. The PFMs provide constant support to the pelvic organs, requiring continuous muscle tone to maintain this support. The most common forms of pelvic floor dysfunction (PFD) occur when the PFMs become weakened at rest, or their ability to react to events of increased abdominal pressure is diminished. PFM weakness or trauma can lead to an excessive urethral excursion, measured as the urethral angle change during Valsalva.

SUMMARY

Provided in accordance with aspects of the present disclosure is a glove-mountable system for pelvic floor muscle (PFM) examination including a first flexible member configured to be secured to an examination glove. The first flexible member includes a force sensor configured to detect a force applied to a PFM of a patient by a user. A second flexible member is configured to be secured to the examination glove. The second flexible member configured to be stacked on the first flexible member when the first and second flexible members are secured to the examination glove. The second flexible member includes an electromyography (EMG) electrode, a stimulation electrode, and a 3-D digitization probe. An actuation button is configured to be actuated by the user when at least one point of interest is detected in at least on PFM. A computer including a processor and a memory is in communication with the first flexible member, the second flexible member and the actuation button. The memory stores computer instructions configured to instruct the processor to generate a 3-D map of a plurality of PFMs of the patient based on data received from the first flexible member, the second flexible member and the actuation button.

In an aspect of the present disclosure, the second flexible member stacked on the first flexible member is an outer layer with respect to the user.

In an aspect of the present disclosure, a control device is in electrical communication with the first flexible member, the second flexible member and the actuation button. The control device includes a signal amplification module configured to amplify a signal received from the first or second flexible members. The control device includes a muscle stimulation module configured to deliver an electrical stimulation to the stimulation electrode.

In an aspect of the present disclosure, the first flexible member is configured to capture force data and communicate the force data to the computer. The second flexible member is configured to capture at least one of EMG data, motor point location data or trigger point location data and communicate at least one of the EMG data, the motor point location data or the trigger point location data to the computer.

In an aspect of the present disclosure, the 3-D map of the plurality of PFMs of the patient is a 3-D point cloud of the plurality of PFMs of the patient generated using data received from the 3-D digitization probe.

In an aspect of the present disclosure, the 3-D point cloud is overlaid on a 3-D model of a PFM anatomy of the patient.

In an aspect of the present disclosure, the 3-D point cloud includes a trigger point map including locations of trigger points identified by the user.

In an aspect of the present disclosure, the 3-D point cloud includes a pain map including locations where pain was reported by the patient.

In an aspect of the present disclosure, the 3-D point cloud includes an EMG map including data of PFM activity detected by the EMG electrode as a result of muscle stimulation by the stimulation electrode or palpation by the user.

In an aspect of the present disclosure, the 3-D point cloud includes a myofascial trigger point map including locations of myofascial trigger points identified by the user.

In an aspect of the present disclosure, the computer instructions stored in the memory of the computer are configured to instruct the processor to diagnose overactive PFM activity or underactive PFM activity and recommend a treatment regimen.

In an aspect of the present disclosure, the recommended treatment regimen includes at least one botulinum toxin injection for treating overactive PFM activity.

Provided in accordance with aspects of the present disclosure is a method of PFM examination including providing a glove-mounted PFM apparatus. The method includes performing, by the user, a vaginal or rectal exam using the glove-mounted PFM apparatus by palpating a plurality of PFMs of the patient. The method includes detecting, by the force sensor, a force applied by the user to each of the plurality of PFMs of the patient. The method includes actuating the actuation button, by the user, when a trigger point or a pain point is identified during palpation of each of the plurality of PFMs of the patient. The method includes determining, by the 3-D digitization probe, a map point for each identified trigger point and each identified pain point. The method includes capturing, by the EMG electrode, data of muscle activity in a particular PFM associated with each identified trigger point and each identified pain point. The method includes generating a 3-D map including map points for each identified trigger point and each identified pain point. The 3-D map includes the data captured by the EMG electrode indicative of the muscle activity in the particular PFM associated with each identified trigger point and each identified pain point.

In an aspect of the present disclosure, the method includes identifying at least one myofascial trigger point and determining, by the 3-D digitization probe, a map point for the identified at least one myofascial trigger point, wherein the generated 3-D map includes the map point for the identified at least one myofascial trigger point.

In an aspect of the present disclosure, the method includes amplifying a signal received from the first or second flexible members.

In an aspect of the present disclosure, the method includes stimulating at least one PFM of the patient by a stimulation electrode included on the second flexible member and recording EMG data, by the EMG probe, of muscle activity resulting from the stimulation applied by the stimulation electrode.

In an aspect of the present disclosure, the method includes performing at least one follow up vaginal or rectal exam using the glove-mounted PFM apparatus, and assessing the effectiveness of the recommended treatment regimen based on the at least one follow up vaginal or rectal exam.

BRIEF DESCRIPTION OF THE DRAWINGS

Various aspects and features of the present disclosure are described hereinbelow with reference to the drawings wherein:

FIG. 5A is a block diagram of another method of PFM examination according to aspects of the present disclosure;

FIG. 6 is a block diagram of another method of PFM examination according to aspects of the present disclosure;

DETAILED DESCRIPTION

Figure 1:
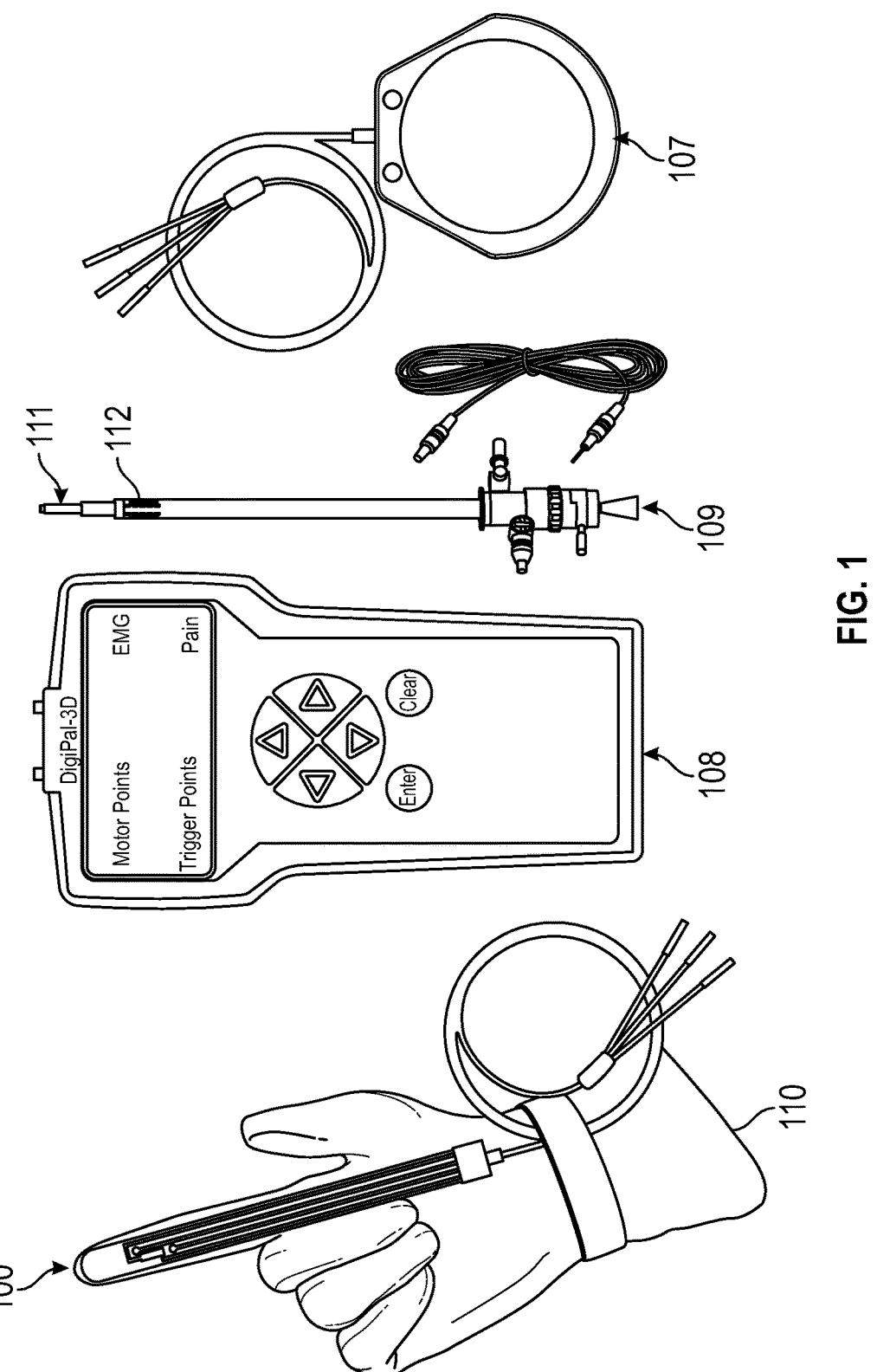
FIG. 1 illustrates a glove-mountable system for PFM examination according to aspects of the present disclosure.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Chronic pelvic pain (CPP), defined as persistent pain in the lower abdomen or the pelvis without an obvious ongoing disease process, is estimated to affect up to 20% of women and 4.2% of men in the US. Pelvic floor hypertonicity (PFH), characterized by an increase in the tonic activity of a pelvic floor muscle, is a symptom related to myofascial pain that presents in up to 85% of patients with interstitial cystitis/bladder pain syndrome (IC/BPS), up to 90% of vulvodynia, as well as a substantial portion of irritable bowel syndrome (IBS) and endometriosis. PFH presents as spastic, constantly shortened pelvic floor muscles and impedes the ability to void or defecate properly. Furthermore, it negatively impacts the sexual quality of life. The etiology of PFH is associated with direct muscle injuries such as obstetric trauma, instrumented delivery, or pelvic surgery, as well as overuse injuries that can occur due to IBS, obstructive defecation, or anxiety.

Conventional surface EMG technology is incapable of comprehensively assessing the neuromuscular function of the PFM because of the complicated anatomy and only provides a single reading for all of the pelvic floor muscles. The present disclosure provides a reliable technique to quantitatively assess and map mechanistic musculoskeletal alterations of muscles to improve the diagnosis of PFD patients for an appropriate treatment protocol.

Figure 2:
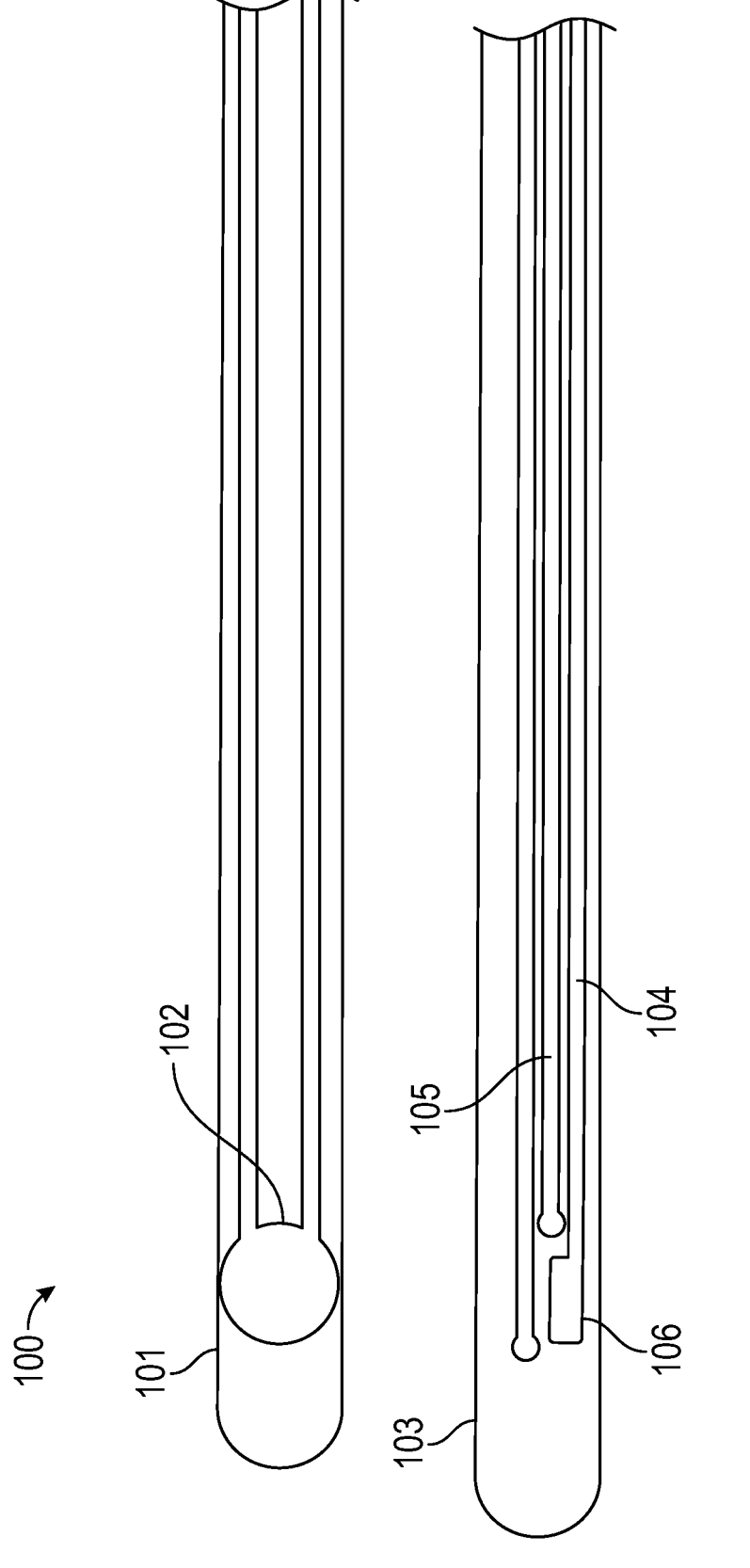
FIG. 2 is an enlarged view of first and second flexible members of the glove-mountable system of FIG. 1.
Figure 3:
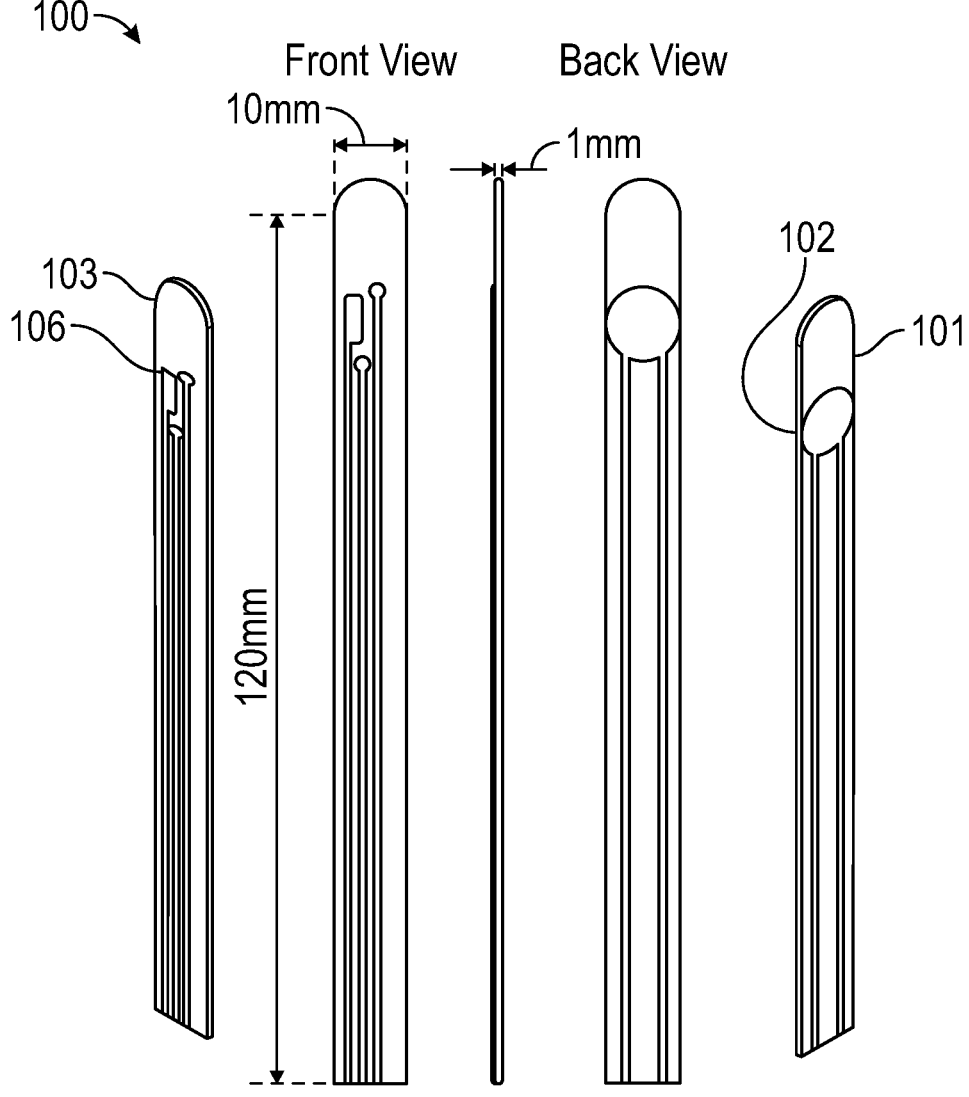
FIG. 3 is a schematic view of the first and second flexible members of the glove-mountable system of FIG. 1.

Referring to FIGS. 1-3, a glove-mounted apparatus includes a force transducer, EMG electrode, muscle stimulation electrode, and 3-D digitizer. The apparatus includes flexible base members, and the top of the apparatus can be bent over the tip of the operator's finger. The apparatus can be secured in this position with, for example, medical adhesive tape. The glove apparatus may be connected to a relatively small battery-powered base-station which provides signal amplification and muscle stimulation. The base station may be connected via USB to a laptop or other similar computer running software to summarize digital pelvic exam findings.

In use, the device and finger is inserted rectally or vaginally, depending on the application. A pelvic exam is performed which can be guided by, for example, three software modules. The software modules guide the collection of trigger point, force, motor point, and EMG data. The software integrates data related to muscle pain, force, motor point, myofascial trigger point, and electromyographic information into a 3-D point cloud, which are combined with a template pelvic 3-D pelvic model to provide localized muscle targets for diagnosis and treatment. By combining this information from diverse anatomical sources, the apparatus and method described herein can develop a comprehensive map of PFM health to guide diagnosis and treatment.

The electrode apparatus includes a flexible printed circuit including a force transducer, EMG recording electrode, stimulation electrode, and a digitization probe. The base station may include an instrumentation amplifier, stimulator, and USB interface. The software stored in the base station includes a 3-D model of the pelvic floor, 3-D point cloud of neuromuscular properties defined during the digital pelvic exam, and a patient management system.

The devices, systems and methods described herein allow for non-invasively localizing pelvic muscle motor point distributions in vivo by employing a motor point imaging technique that can provide critical information for guiding the precision injection of chemodenervating injections for optimal treatment outcomes by implementing stimulation electrode pelvic muscle motor point distribution information.

With continued reference to FIGS. 1-3 glove-mountable system for pelvic floor muscle (PFM) examination 100 includes a first flexible member 101 configured to be secured to an examination glove 110. The first flexible member 101 includes a force sensor 102 configured to detect a force applied to a PFM of a patient by a user. A second flexible member 103 is configured to be secured to the examination glove. The second flexible member 103 is configured to be stacked on the first flexible member 101 when the first and second flexible members 101 and 103 are secured to the examination glove 110. As an example, the second flexible member 103 stacked on the first flexible member 101 is an outer layer with respect to the user. The second flexible member 103 includes an electromyography (EMG) electrode 104, a stimulation electrode 105, and a 3-D digitization probe 106. The first or second flexible members 101 or 101 may include or may be arranged on a flexible substrate that is a relatively thin, heat-resistant material made from or including polymers such as polyimide and polyethylene terephthalate (PET). As an example, the first flexible member 101 is arranged on a first side of the flexible substrate and the second flexible member 103 is arranged on a second side of the flexible substrate. Thus, a single flexible substrate can support each of the first flexible member 101 and the second flexible member 103.

According an aspect of the present disclosure, a force transducer module may be arranged on a first side of a flexible substrate and a muscle stimulation/recording electrode module may be arranged on a second side of the flexible substrate opposite the first side. Thus, a single flexible substrate can support each of the modules and the single flexible substrate can be mounted to a user's gloved finger for used as described herein. As an example, the modules may be printed onto opposite sides of a single flexible printed circuit.

The force transducer (see, e.g., force sensor 102) is configured to be in contact with a user's finger, and the EMG recording/stimulation electrode (see, e.g., electrodes 104 and 105) is configured to be in contact with a patient's body.

An actuation button 107 is configured to be actuated by the user when at least one point of interest is detected in at least on PFM. The actuation button 107 may be a foot actuated button (see, e.g., FIG. 1) that is activated by a user/clinician during a PFM examination. The user may activate the actuation button 107 each time pain is reported by a patient in a particular muscle being palpated by the user/clinician. The user may activate the actuation button 107 each time a trigger point (e.g., an irregular region of a muscle such as a bump or protrusion) is felt during palpation. Data is recorded by the electrodes and probes described herein each time the actuation button 107 is activated and used to generate the 3-D map of PFMs of the patient.

A computer (see, e.g., computer 700 described below) including a processor and a memory is in communication with the first flexible member 101, the second flexible member 103 and the actuation button 107. The memory stores computer instructions configured to instruct the processor to generate a 3-D map of a plurality of PFMs of the patient based on data received from the first flexible member 101, the second flexible member 103 and the actuation button 107.

A control device 108 (see, e.g., FIG. 1) is in electrical communication with the first flexible member 101, the second flexible member 103 and the actuation button 107 (e.g., via a wired or wireless connection). The control device 108 includes a signal amplification module configured to amplify a signal received from the first or second flexible members 101 or 103. The control device 108 includes a muscle stimulation module configured to deliver an electrical stimulation to the stimulation electrode 105.

The first flexible member 101 is configured to capture force data and communicate the force data to the computer 700. Force data is indicative of an amount of pressure applied by a user/clinician to a particular PFM during palpation, such that a quantitative assessment of a force required to elicit pain or trigger a muscle spasm can be identified. A finding of a relatively low force triggering a muscle spasm may be indicative of an overactive PFM, and a finding of a relatively high force needed to trigger a muscle may be indicative of an underactive PFM.

The second flexible member 103 is configured to capture at least one of EMG data, motor point location data or trigger point location data and communicate at least one of the EMG data, the motor point location data or the trigger point location data to the computer 700.

Figure 5B:
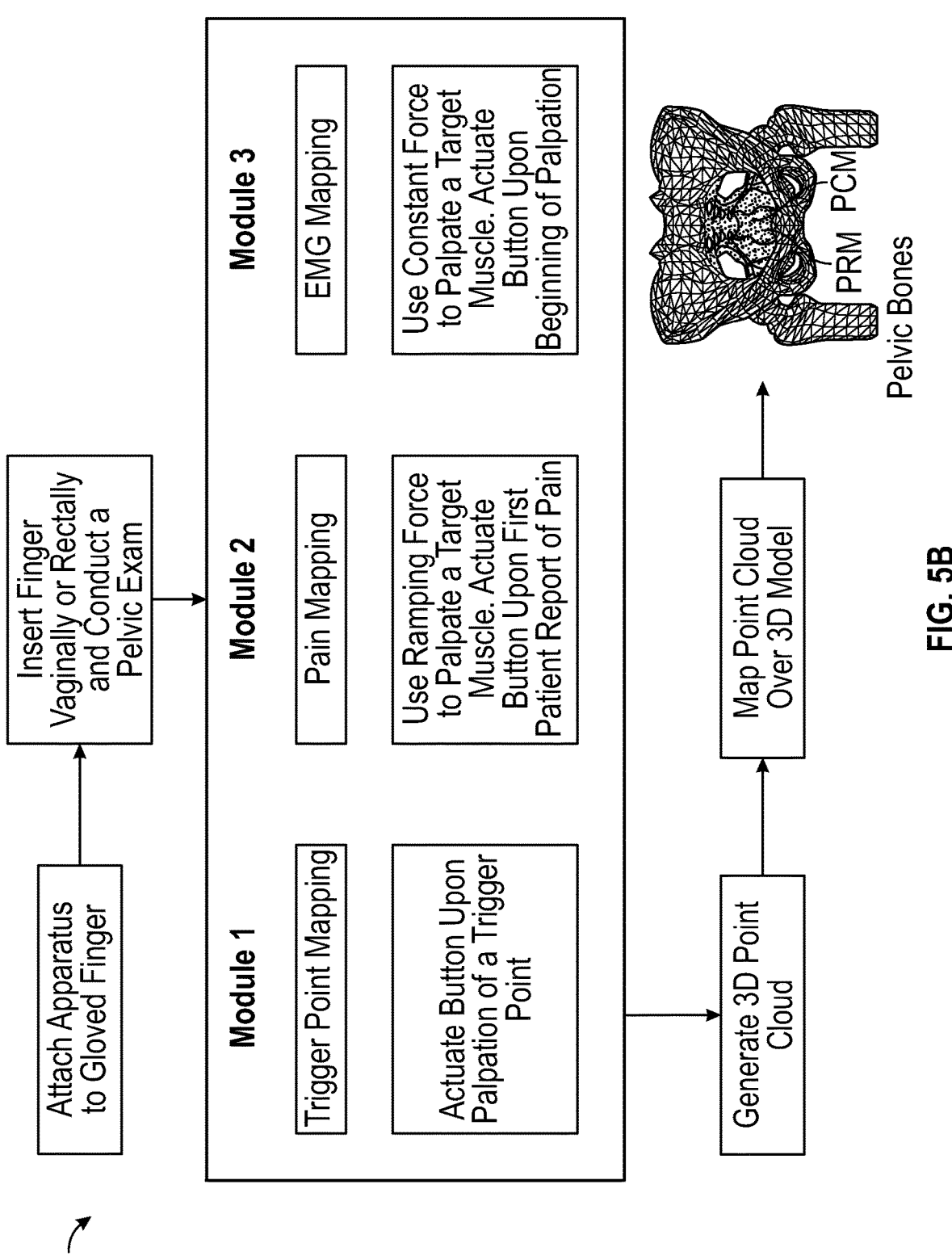
FIG. 5B is a block diagram of another method of PFM examination according to aspects of the present disclosure.

In an aspect of the present disclosure, the 3-D map of the plurality of PFMs of the patient is a 3-D point cloud of the plurality of PFMs of the patient generated using data received from the 3-D digitization probe (see, e.g., FIGS. 5A and 5B).

In an aspect of the present disclosure, the 3-D point cloud is overlaid on a 3-D model of a PFM anatomy of the patient.

In an aspect of the present disclosure, the 3-D point cloud includes a trigger point map including locations of trigger points identified by the user.

In an aspect of the present disclosure, the 3-D point cloud includes a motor point map including locations of trigger points identified by the user.

In an aspect of the present disclosure, the 3-D point cloud includes a pain map including locations where pain was reported by the patient.

In an aspect of the present disclosure, the 3-D point cloud includes an EMG map including data of PFM activity detected by the force transducer or EMG electrode as a result of muscle stimulation by the stimulation electrode or palpation by the user.

In an aspect of the present disclosure, the 3-D point cloud includes a motor point map including data of PFM activity detected by the force transducer or EMG electrode as a result of muscle stimulation by the stimulation electrode by the user.

In an aspect of the present disclosure, the 3-D point cloud includes a myofascial trigger point map including locations of myofascial trigger points identified by the user.

The devices, systems and methods described herein can be employed to diagnose a PFM disorder, such as overactive PFM activity or underactive PFM activity and recommend a treatment regimen. As an example, the recommended treatment regimen may include at least one botulinum toxin injection for treating overactive PFM activity.

Figure 4:
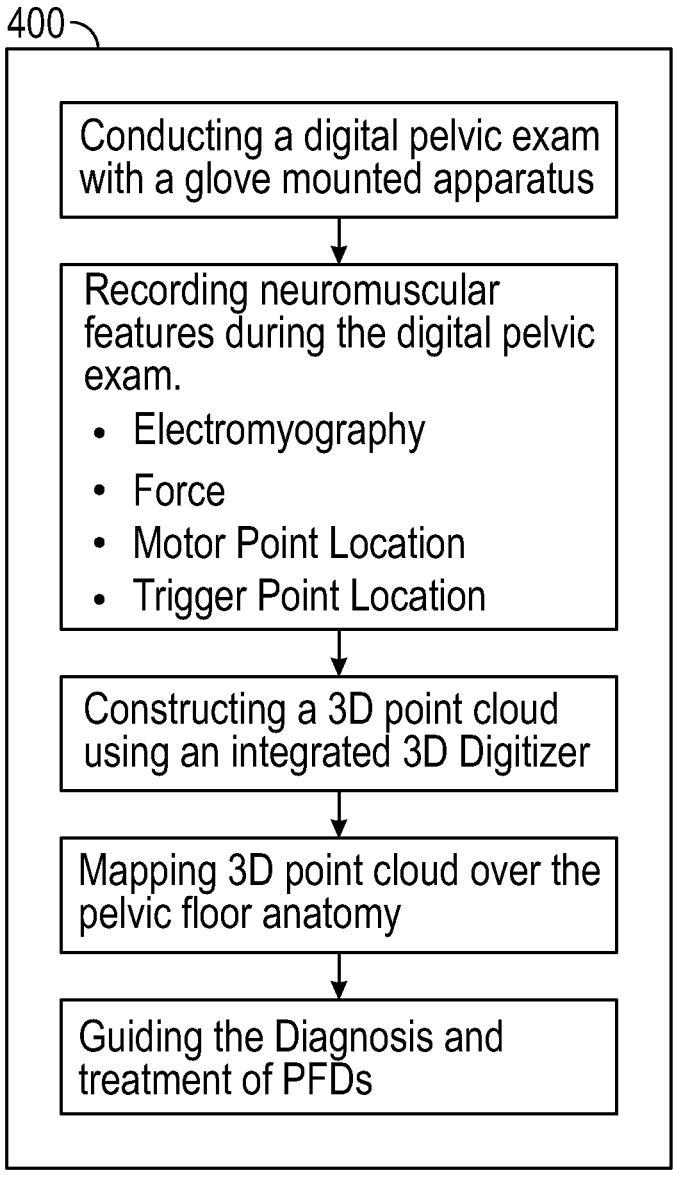
FIG. 4 is a block diagram of a method of PFM examination according to aspects of the present disclosure.

FIG. 4 describes a method 400 of palpating PFMs in a patient be employing the glove-mounted system and apparatus described herein the guide the diagnosis and treatment of PFDs.

Referring to FIG. 4, an examination may be performed by a clinician/user to diagnose and treat PFDs by using the glove-mounted apparatus and system described herein.

FIG. 5A and FIG. 5B each describe a method 500, 501 of 3-D mapping including a series of algorithms that may be included in the computer instructions employed by the computer described herein.

Referring to FIGS. 5A and 5B, a 3-D point cloud map is generated using data captured using the glove-mounted apparatus and system described herein.

FIG. 6 describes a method 600 of PFM examination including providing a glove-mounted PFM apparatus.

Referring to FIG. 6, the method 600 of PFM examination includes the user/clinician performing a vaginal or rectal exam using the glove-mounted PFM apparatus by palpating a plurality of PFMs of the patient. The force sensor detects an amount of force applied by the user to each of the plurality of PFMs of the patient. When a trigger point or a pain point is identified during palpation of each of the plurality of PFMs of the patient by the user/clinician, the user/clinician will activate the actuation button. Activating the actuation button creates a map point and triggers data capture by the electrodes and probes of the examination apparatus. As an example, the user/clinician will activate the actuation button each time a patient reports pain or each time the clinician identifies a trigger point and any abnormality for use in generating a 3-D map.

The 3-D digitization probe determines a map point for each identified trigger point and each identified pain point. The EMG electrode captures data of muscle activity in a particular PFM associated with each identified trigger point and each identified pain point. Muscle activity may be trigger by palpation, voluntary contraction or direct electrical stimulation. A 3-D map including map points for each identified trigger point and each identified pain point is generated. The 3-D map includes the data captured by the EMG electrode indicative of the muscle activity in the particular PFM associated with each identified trigger point and each identified pain point.

In an aspect of the present disclosure, the method of PFM examination includes identifying at least one myofascial trigger point and determining, by the 3-D digitization probe, a map point for the identified at least one myofascial trigger point, wherein the generated 3-D map includes the map point for the identified at least one myofascial trigger point.

In at least some cases, a signal received from the first or second flexible members 101 or 103 can be amplified by the control module 108 described herein.

In an aspect of the present disclosure, the method of PFM examination includes stimulating at least one PFM of the patient by the stimulation electrode 105 included on the second flexible member 103 and recording EMG data, by the EMG probe 104, of muscle activity resulting from the stimulation applied by the stimulation electrode 105.

At least one follow up vaginal or rectal exam using the glove-mounted PFM apparatus may be performed to assess the effectiveness of the recommended treatment regimen based on the at least one follow up vaginal or rectal exam.

With ongoing reference to FIG. 6, a motor point assessment may also be performed by the Examiner. The examiner palpates a target muscle and electrically stimulates muscle via the apparatus. If an elicited twitch is detected via force response, the examiner can actuate the button and "log" the location of the motor point.

Figure 7:
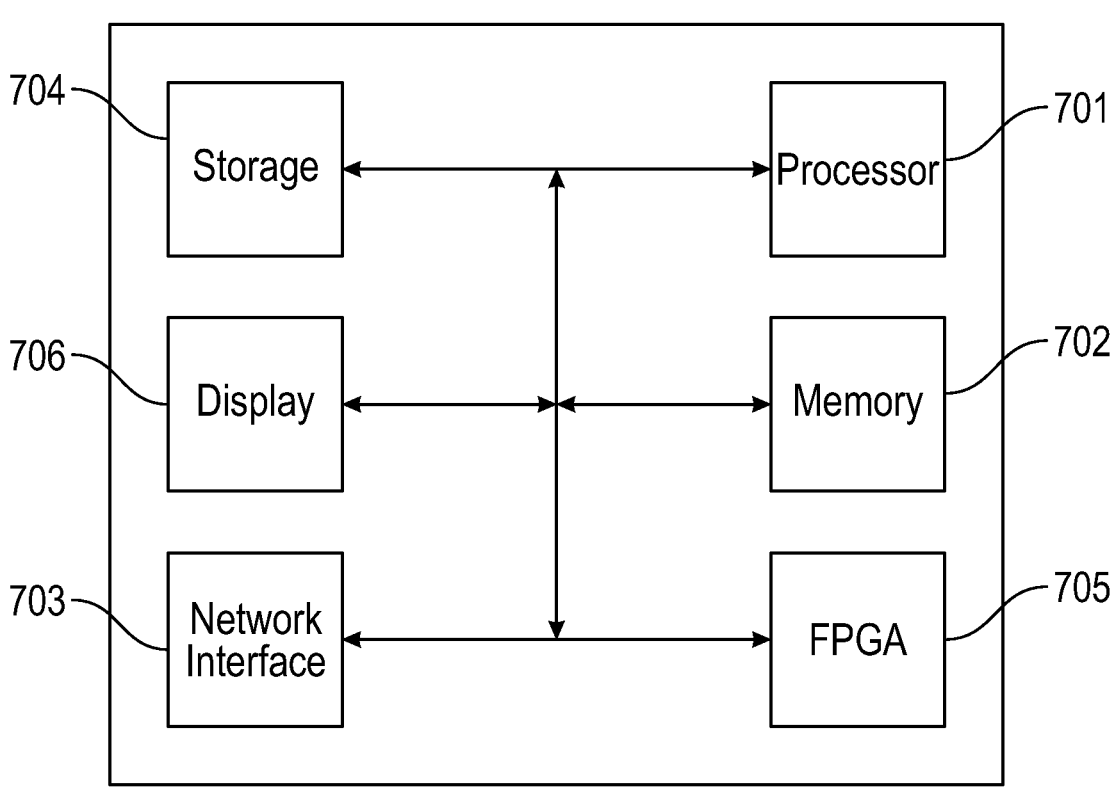
FIG. 7 is a block diagram of an exemplary computer of the system of FIG. 1 according to aspects of the present disclosure.

FIG. 7 is a block diagram of an exemplary computer 700 of the system of FIG. 1 according to aspects of the present disclosure.

Referring to FIG. 7, the computer 700 may include a display 706 and a processor 701 connected to a computer-readable storage medium or a memory 702 which may be a volatile type memory, e.g., RAM, or a non-volatile type memory, e.g., flash media, disk media, etc. The processor 701 may be another type of processor such as, without limitation, a digital signal processor, a microprocessor, an ASIC, a graphics processing unit (GPU), field-programmable gate array (FPGA), or a central processing unit (CPU).

In some aspects of the disclosure, the memory 702 can be random access memory, read-only memory, magnetic disk memory, solid state memory, optical disc memory, and/or another type of memory. The memory 702 can communicate with the processor 701 through communication buses of a circuit board and/or through communication cables such as serial ATA cables or other types of cables. The memory 702 includes computer-readable instructions that are executable by the processor 701 to operate the control unit 108. The computer 700 may include a network interface 703 (e.g., a wireless network interface) to communicate with other computers or a server. A storage device 704 may be used for storing data. The computer may include one or more FPGAs 705. The FPGA 705 may be used for executing various machine learning algorithms.

In an aspect of the present disclosure, the computer 700 is wirelessly connected with the sensors of the first or second flexible members. Alternatively, the computer 700 may be connected with the sensors of the first or second flexible members via a wired connection (e.g., a USB connection). As an example, the computer 700 may be included in a smartphone or tablet computer. The computer 700 may also be a laptop or desktop computer in communication with the EMG amplifier. The computer 700 may also be housed in a special purpose control device (see, e.g., FIG. 1).

Figure 8A:
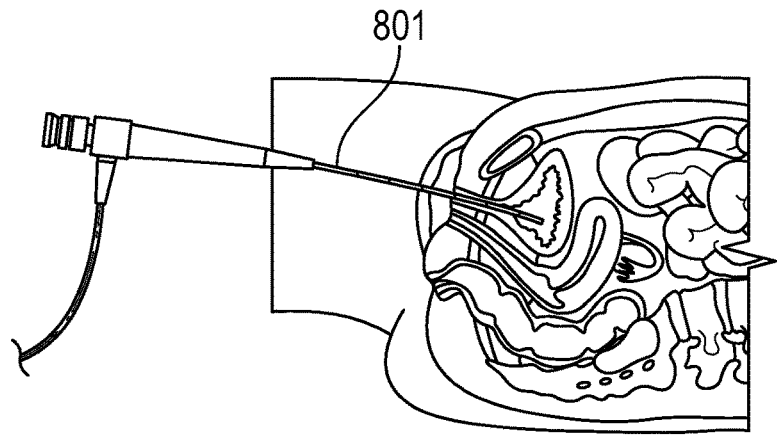
FIGS. 8A and 8B illustrate a catheter mounted pressure sensor and surface EMG sensor over the tip of the catheter for motor point location in the bladder.
Figure 8B:
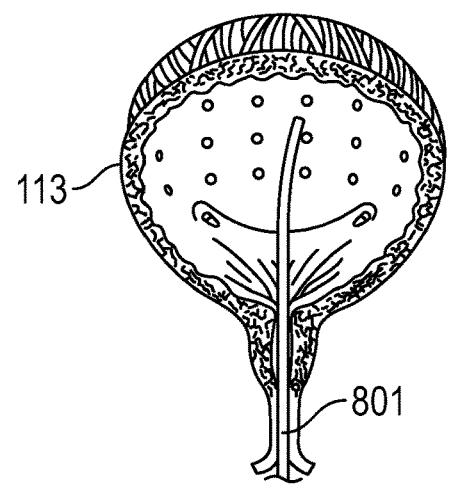

FIGS. 8A and 8B illustrate a catheter 801 mounted pressure sensor and surface EMG sensor (see, e.g., FIG. 8C) over the tip of the catheter 801 for motor point localization in the bladder 113.

Referring to FIGS. 8A and 8B, the catheter 801 mounted pressure sensor can be employed for motor point localization over the detrusor muscle to guide BoNT injection for treating a bladder disorder in a patient. A 3-D map of the patient's bladder and associated muscles may be generated by employing the devices, systems and methods described herein.

Figure 8C:
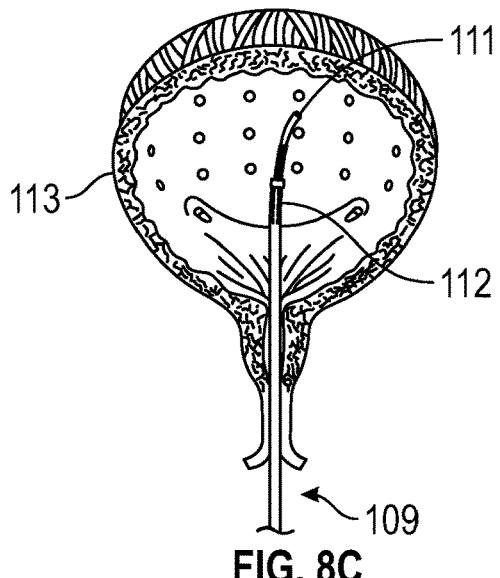
FIG. 8C illustrates a cystoscope mounted pressure sensor and surface EMG sensor over the tip of the cystoscope for motor point location in the bladder.

FIG. 8C illustrates a cystoscope 109 mounted pressure sensor 111 and surface EMG sensor 112 over the tip of the cystoscope 109 for motor point location in the bladder 113.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A glove-mountable system for pelvic floor muscle (PFM) examination, comprising:
    a first flexible member configured to be secured to an examination glove, the first flexible member including a force sensor configured to detect a force applied to a PFM of a patient by a user;
    a second flexible member configured to be secured to the examination glove, the second flexible member being separately attachable from the first flexible member and configured to be stacked directly over the first flexible member in a glove-mounted configuration that preserves tactile sensitivity, the second flexible member including an integrated array comprising an electromyography (EMG) electrode, a stimulation electrode, and a 3-D digitization probe configured to determine spatial coordinates of palpated PFM locations in real time;

an actuation button configured to be actuated by the user when at least one point of interest is detected in at least one PFM; and a computer including a processor and a memory in communication with the first flexible member, the second flexible member and the actuation button, the memory storing computer instructions configured to instruct the processor to a use the force data, EMG data, stimulation-evoked responses, and digitization-probe-derived spatial coordinates to generate a patient-specific 3-D map of a plurality of PFMs of the patient.

2. The system of claim 1, wherein the second flexible member stacked on the first flexible member is an outer layer with respect to the user.

3. The system of claim 1, further including a control device in electrical communication with the first flexible member, the second flexible member and the actuation button, the control device including a signal amplification module configured to amplify a signal received from the first or second flexible members, and the control device including a muscle stimulation module configured to deliver an electrical stimulation to the stimulation electrode.

4. The system of claim 1, wherein the first flexible member is configured to capture force data and communicate the force data to the computer, and wherein the second flexible member is configured to capture at least one of EMG data, motor point location data or trigger point location data and communicate at least one of the EMG data, the motor point location data or the trigger point location data to the computer.

5. The system of claim 1, wherein the 3-D map of the plurality of PFMs of the patient is a 3-D point cloud of the plurality of PFMs of the patient generated using data received from the 3-D digitization probe.

6. The system of claim 5, wherein the 3-D point cloud is overlaid on a 3-D model of a PFM anatomy of the patient.

7. The system of claim 6, wherein the 3-D point cloud includes a trigger point map including locations of trigger points identified by the user.

8. The system of claim 6, wherein the 3-D point cloud includes a pain map including locations where pain was reported by the patient.

9. The system of claim 6, wherein the 3-D point cloud includes an EMG map including data of PFM activity detected by the EMG electrode as a result of muscle stimulation by the stimulation electrode or palpation by the user.

10. The system of claim 6, wherein the 3-D point cloud includes a myofascial trigger point map including locations of myofascial trigger points identified by the user.

11. The system of claim 1, wherein the computer instructions stored in the memory of the computer are configured to instruct the processor to diagnose overactive PFM activity or underactive PFM activity and recommend a treatment regimen.

12. The system of claim 11, wherein the recommended treatment regimen includes at least one botulinum toxin injection for treating overactive PFM activity.

* * * * *